United States Patent

Becker et al.

[11] Patent Number: 4,837,346
[45] Date of Patent: Jun. 6, 1989

[54] PREPARATION OF ESTERS OF TETRAHYDROPYRAN-4-CARBOXYLIC ACID

[75] Inventors: Rainer Becker, Bad Durkheim; Heinz Eckhardt, Ludwigshafen; Rolf Fischer, Heidelberg; Wolfgang Spiegler, Worms; Uwe Vagt, Speyer, all of Fed. Rep. of Germany

[73] Assignee: BASF Aktiengesellschaft, Ludwigshafen, Fed. Rep. of Germany

[21] Appl. No.: 170,768

[22] Filed: Mar. 21, 1988

[30] Foreign Application Priority Data

Mar. 31, 1987 [DE] Fed. Rep. of Germany ....... 3710805

[51] Int. Cl.$^4$ ........................................... C07D 309/06
[52] U.S. Cl. ................................................... 549/425
[58] Field of Search ......................................... 549/425

[56] References Cited
PUBLICATIONS

J. Chem. Soc., (1930) pp. 2525–2530.

Primary Examiner—Nicky Chan
Attorney, Agent, or Firm—John H. Shurtleff

[57] ABSTRACT

A process for the preparation of esters of tetrahydropyran-4-carboxylic acid of the general formula I, where $R^1$ is an alkyl, cycloalkyl, or aryl group, by treating butyrolactones of the general formula II, where $R^2$ is a hydrogen atom, an alkyl group, or an acyl group —CO—$R^3$, $R^3$ being a hydrogen atom or an alkyl group with from 1 to 6 carbon atoms, with alcohols of the general formula III at temperatures of from 150° C. to 400° C. in the presence of acid catalysts.

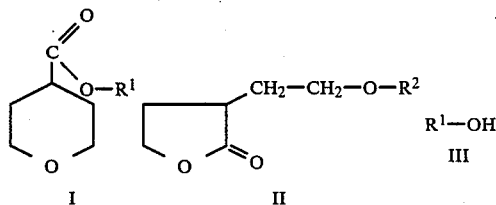

5 Claims, No Drawings

PREPARATION OF ESTERS OF TETRAHYDROPYRAN-4-CARBOXYLIC ACID

The present invention relates to a process for the preparation of esters of tetrahydropyran-4-carboxylic acid by the reaction of 3-(2-hydroxyethyl)butyrolactone or esters and ethers thereof with alcohols in the presence of an acid catalyst.

According to the statements in *J. Chem. Soc.*, 2525–30 (1930) esters of tetrahydropyran-4-carboxylic acid can be prepared by treating 2,2'-dichlorodiethyl ether with the sodium salt of diethyl malonate to form diethyl tetrahydropyran-4,4-dicarboxylate, hydrolyzing to obtain tetrahydropyran-4,4-dicarboxylic acid, decarboxylating to tetrahydropyran-4-carboxylic acid, and finally esterifying.

The object was to develop a simpler, economic process for the preparation of esters of tetrahydropyran-4-carboxylic acid.

This object is achieved by the novel process, by which esters of tetrahydropyran-4-carboxylic acid of the general formula I—where $R^1$ is an alkyl group of from 1 to 6 carbon atoms, a cycloalkyl group of from 5 to 7 carbon atoms, or an aryl group of from 6 to 10 carbon atoms—can be prepared particularly advantageously by treating butyrolactones of the general formula II—where $R^2$ is a hydrogen atom, an alkyl group with from 1 to 6 carbon atoms, or an acyl group —CO—$R^3$, $R^3$ being a hydrogen atom or an alkyl group with from 1 to 6 carbon atoms—with alcohols of the general formula III—where $R^1$ has the meaning given above—at temperatures of from 150° C. to 400° C. in the presence of acid catalysts.

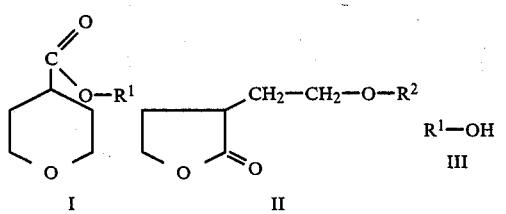

It could not be foreseen that esters of tetrahydropyran-4-carboxylic acid would be formed with good selectivity from 3-(2-hydroxyethyl)butyrolactone or its derivatives and alcohols, since many competing reactions leading to other products could have taken place.

The novel reaction can be displayed by the following equation, which is for the formation of methyl tetrahydropyran-4-carboxylate from 3-(2-hydroxyethyl)butyrolactone and methanol:

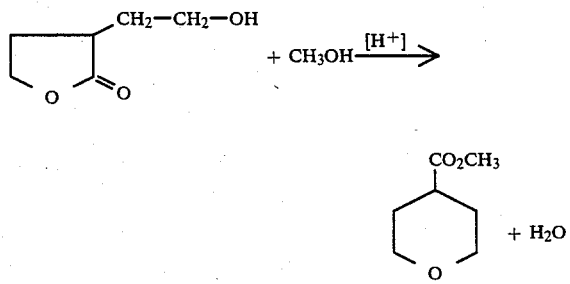

Suitable lactones of the general formula II include 3-(2-hydroxyethyl)butyrolactone, its methyl, ethyl, propyl, or butyl ethers, and its esters with formic, acetic, propionic, butyric, valeric, and isovaleric acids. Suitable alcohols of the general formula III are methanol, ethanol, 1-propanol, 2-propanol, 2-methyl-2-propanol, 1-butanol, 2-methyl-1-propanol, 2-butanol, 1-pentanol, 1-hexanol, phenol, cyclopentanol, and cyclohexanol, for example. Methanol, ethanol, and propanols are especially suitable.

The ratio of the amount of butyrolactone II to the amount of alcohol III is advantageously from 1:0.5 to 1:10, above all from 1:1 to 1:5. The reaction is carried out at a temperature between 150° C. and 400° C., preferably from 200° C. to 400° C., and above all from 200° C. to 300° C. Pressures of from 1 bar to 100 bar, especially from 1 to 10 bar, are advantageous.

Suitable acid catalysts are the acid oxides of elements of subgroups IIIA and IVA and subgroups IVB, VB, and VIB of the Periodic Table; these are preferred to protonic or Lewis acids. Examples are heterogeneous acid catalysts, such as silica in the forms of silica gel, kieselguhr, and quartz, and also titanium dioxide, zirconium dioxide, phosphorus pentoxide, vanadium pentoxide, boron trioxide, aluminum oxide, chromium oxides, molybdenum oxides, tungsten oxides, or mixture of these. Zeolites, e.g. Y zeolites, are also suitable.

The butyrolactones II can be converted conveniently in the gas phase over such fixed-bed catalysts. It is then advantageous to work with catalyst loads (mass of butyrolactone per hour per unit mass of catalyst) of from 0.1 h$^{-1}$ to 10 h$^{-1}$, above all from 0.1 h$^{-1}$ to 5 h$^{-1}$.

The reaction can be carried out batchwise or continuously in the liquid or gas phase with fixed-bed catalysts, by the ascending flow or trickle procedures, for instance, in a fluidized bed, or in the liquid phase with suspended fixed-bed catalysts. It is however also possible to employ acid catalysts that are dissolved homogeneously in the liquid phase. Suitable acid catalysts include mineral acids, such as sulfuric, phosphoric, hydrochloric, nitric, or hydrobromic acids, and sulfonic acids such as benzenesulfonic and p-toluenesulfonic acids. The ratio of the amount of butyrolactone II to the amount of acid can be, for instance, from 1:0.001 to 1:1, particularly from 1:0.01 to 1:0.1.

The reaction of the butyrolactones with the alcohols in the liquid phase is typically carried out by heating a mixture of the lactone and the required alcohol to the chosen reaction temperature in the presence of a suspended fixed-bed catalyst or a homogeneously dissolved catalyst. At the end of the necessary reaction time the mixture is cooled and the acid catalyst is removed, for instance by filtration or neutralization. Finally the reaction mixture is fractionally distilled to isolate the desired ester of tetrahydropyran-4-carboxylic acid.

In a preferred embodiment of the novel process of the gas phase a mixture of the butyrolactone and the required alcohol is vaporized, diluted if necessary with an inert gas such as nitrogen, carbon dioxide, or argon, and passed over a fixed catalyst arrangement at the required temperature; it is an advantage if the catalyst is kept in turbulent motion up and down. The product of the reaction is condensed by cooling and then fractionally distilled. The desired ester of tetrahydropyran-4-carboxylic acid is isolated; unreacted hydroxyethylbutyrolactone or its ethers or esters can be returned to the reaction.

3-(2-Hydroxyethyl)butyrolactone can be prepared, for example, from ethyl acetoacetate and ethylene oxide.

The esters that can be prepared by the novel process are valuable intermediates, which can be converted into the sought-after tetrahydropyran-4-carbaldehyde, for example.

EXAMPLE 1

(a) A solution consisting of 52% 3-(2-hydroxyethyl)-butyrolactone, 38% methanol, and 10% water—the proportions being mass fractions—was pumped at the rate of 100 ml/h into an evaporator at 300° C., and the vapor was mixed with a stream of nitrogen flowing at 175 l/h and passed over 300 g (350 ml) of aluminum oxide fluidized-bed catalyst (particle size from 0.1 mm to 0.3 mm) at a reaction temperature of 270° C. The experiment was continued for 12.5 h, during which time 650 g (5.0 mol) of the hydroxyethylbutyrolactone was employed. The gaseous reaction mixture was condensed in cold traps and fractionally distilled at reduced pressure. The following three fractions were obtained in the yields stated:

Fraction 1: 260 g (36% yield) methyl tetrahydropyran-4-carboxylate, b.p. 86°–90° C./24 mbar Fraction 2: 162 g (29% yield) 3-vinylbutyrolactone, b.p. 105°–109° C./24 mbar Fraction 3: 144 g (20% yield) 3-methoxyethylbutyrolactone, b.p. 137° C./24 mbar Fractions 2 and 3 were re-employed as described below.

(b) A solution consisting of 52% 3-methoxyethyl-butyrolactone, 38% methanol, and 10% water—the proportions being mass fractions—was pumped at the rate of 100 ml/h into an evaporator at 300° C., and the vapor was mixed with a stream of nitrogen flowing at 175 l/h and passed over 300 g (350 ml) of aluminum oxide fluidized-bed catalyst (particle size from 0.1 mm to 0.3 mm) at a reaction temperature of 270° C. The experiment was continued for 3 h, during which time 144 g (1.0 mol) of 3-methoxyethylbutyrolactone derived from Fraction 3 was employed. The gaseous reaction mixture was condensed in cold traps and fractionally distilled at reduced pressure. The following three fractions were obtained in the yields stated:

Fraction 1: 37 g (26% yield) methyl tetrahydropyran-4-carboxylate, b.p. 86°–90° C./24 mbar Fraction 2: 34 g (30% yield) 3-vinylbutyrolactone, b.p. 105°–109° C./24 mbar Fraction 3: 45 g (31% yield) 3-methoxyethylbutyrolactone, b.p. 137° C./24 mbar (c) A solution consisting of 52% 3-vinylbutyrolactone, 38% methanol, and 10% water—the proportions being mass fractions—was pumped at a rate of 100 ml/h into an evaporator at 300° C., and the vapor was mixed with a stream of nitrogen flowing at 175 l/h and passed over 300 g (350 ml) of aluminum oxide fluidized-bed catalyst (particle size from 0.1 mm to 0.3 mm) at a reaction temperature of 270° C. The experiment was continued for 3 h, during which time 162 g (1.45 mol) of 3-vinylbutyrolactone derived from Fraction 2 was employed. The gaseous reaction mixture was condensed in cold traps and fractionally distilled at reduced pressure. The following three fractions were obtained in the yields stated:

Fraction 1: 21 g (10% yield) methyl tetrahydropyran-4-carboxylate, b.p. 86°–90° C./24 mbar Fraction 2: 112 g (69% yield) 3-vinylbutyrolactone, b.p. 105°–109° C./24 mbar Fraction 3: 17 g (8% yield) 3-methoxyethylbutyrolactone, b.p. 137° C./24 mbar The total yields were thus:

Fraction 1: 318 g (44% yield) methyl tetrahydropyran-4-carboxylate, b.p. 86°–90° C./24 mbar Fraction 2: 146 g (26% yield) 3-vinylbutyrolactone, b.p. 105°–109° C./24 mbar Fraction 3: 62 g (9% yield) 3-methoxyethylbutyrolactone, b.p. 137° C.

EXAMPLE 2

(Temperature Dependence)

A solution consisting of 52% 3-(2-hydroxyethyl)-butyrolactone, 38% methanol, and 10% water—the proportions being mass fractions—was pumped at the rate of 100 ml/h into an evaporator at 300° C., and the vapor was mixed with a stream of nitrogen flowing at 175 l/h and passed over 300 g (350 ml) of aluminum oxide fluidized-bed catalyst (particle size from 0.1 mm to 0.3 mm) at the reaction temperatures given in the following table. Each experiment was continued for 4 h. The gaseous reaction mixture was condensed in cold traps and analyzed by gas chromatography. The results are given in the table.

| | Yield of substance/% at | | | | |
|---|---|---|---|---|---|
| | 300° C. | 270° C. | 260° C. | 250° C. | 240° C. |
| Methyl tetrahydropyran-4-carboxylate | 14 | 36 | 41 | 40 | 42 |
| 3-Vinylbutyrolactone | 56 | 27 | 21 | 16 | 16 |
| 3-(2-Methoxyethyl)butyrolactone | 12 | 20 | 20 | 18 | 20 |
| 3-(2-Hydroxyethyl)butyrolactone | below 1 | 4 | 5 | 10 | 10 |

EXAMPLE 3

A solution consisting of 52% 3-(2-hydroxyethyl)-butyrolactone, 38% methanol, and 10% water—the proportions being mass fractions—was pumped at the rate of 150 ml/h into an vaporator, and the vapor was mixed with a stream of nitrogen flowing at 175 l/h and passed over 300 g (350 ml) of aluminum oxide fluidized-bed catalyst (particle size from 0.1 mm to 0.3 mm) at a reaction temperature of 260° C. The experiment was continued for 17 h, during which time 1300 g (10.0 mol) of the hydroxyethylbutyrolactone was employed.

The gaseous reaction mixture was condensed in cold traps and fractionally distilled at reduced pressure. The first fraction collected after separation of methanol and water consisted of pure methyl tetrahydropyran-4-carboxylate, b.p. 90°–93° C./30 mbar.

The mixture remaining in the distilled vessel was then distilled over at reduced pressure and mixed with sufficient methanol and water to produce a 52% solution as before. This solution was brought into the reaction as described above. The whole procedure was then repeated another three times.

The total yield of distilled methyl tetrahydropyran-4-carboxylate was 791 g (55%).

We claim:

1. A process for the preparation of esters of tetrahydropyran-4-carboxylic acid of the general formula I

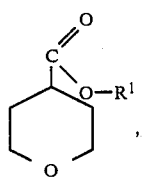

where $R^1$ is an alkyl group of from 1 to 6 carbon atoms, a cycloalkyl group of from 5 to 7 carbon atoms, or an aryl group of from 6 to 10 carbon atoms, by treating butyrolactones of the general formula II,

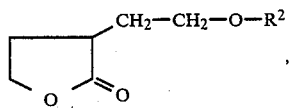

where $R^2$ is a hydrogen atom, an alkyl group of from 1 to 6 carbon atoms, or an acyl group —CO—$R^3$, $R^3$ being a hydrogen atom or an alkyl group of from 1 to 6 carbon atoms, with alcohols of the general formula III, $$R^1\text{—OH} \qquad \text{III,}$$

where $R^1$ has the meaning given above, at temperatures of from 150° C. to 400° C. in the presence of acid catalysts.

2. A process as claimed in claim 1 wherein the reaction is carried out at from 200° C. to 300° C.

3. A process as claimed in claim 1 wherein the catalysts are acidic oxides of elements of subgroups IIIA and IVA and subgroups IVB, VB, and VIB of the Periodic Table.

4. A process as claimed in claim 1 wherein the catalysts are aluminum oxide, silicon dioxide, titanium dioxide, zirconium dioxide, phosphorus pentoxide, vanadium pentoxide, boron trioxide, or oxides of chromium, molybdenum, or tungsten.

5. A process as claimed in claim 1 wherein the reaction of butyrolactones with alcohols is carried out in the presence of catalyst in the gas or liquid phase.

* * * * *